United States Patent [19]

Harms et al.

[11] Patent Number: 5,196,013
[45] Date of Patent: * Mar. 23, 1993

[54] PEDICEL SCREW AND CORRECTING AND SUPPORTING APPARATUS COMPRISING SUCH SCREW

[76] Inventors: Jürgen Harms, Belchenweg 9, Waldbronn-Reichenbach; Lutz Biedermann, Berta-Suttner-Str. 23, D-7730 VS-Schwenningen, both of Fed. Rep. of Germany

[*] Notice: The portion of the term of this patent subsequent to Mar. 3, 2009 has been disclaimed.

[21] Appl. No.: 679,086
[22] PCT Filed: Nov. 2, 1990
[86] PCT No.: PCT/EP90/01834
§ 371 Date: Jun. 28, 1991
§ 102(e) Date: Jun. 28, 1991
[87] PCT Pub. No.: WO91/06254
PCT Pub. Date: May 16, 1991

[30] Foreign Application Priority Data
Nov. 3, 1989 [DE] Fed. Rep. of Germany ....... 3936702

[51] Int. Cl.$^5$ .............................................. A61F 5/04
[52] U.S. Cl. ...................................................... 606/61
[58] Field of Search ...................... 606/53, 54, 72, 73, 606/60, 61

[56] References Cited

U.S. PATENT DOCUMENTS

| | | | |
|---|---|---|---|
| 3,865,105 | 2/1975 | Lode | 606/61 |
| 4,135,505 | 1/1979 | Day | 606/54 X |
| 4,836,196 | 6/1989 | Park et al. | |
| 4,946,458 | 8/1990 | Harms et al. | 606/61 |
| 4,957,495 | 9/1990 | Kluger | 606/61 X |
| 4,987,892 | 1/1991 | Krag et al. | 606/61 |
| 5,002,542 | 3/1991 | Frigg | 606/61 |
| 5,042,982 | 8/1991 | Harms et al. | 606/61 |
| 5,092,867 | 3/1992 | Harms et al. | 606/61 |

FOREIGN PATENT DOCUMENTS

| | | |
|---|---|---|
| 0140786A2 | 5/1985 | European Pat. Off. . |
| 0242708A3 | 10/1987 | European Pat. Off. . |
| 0242708A2 | 10/1987 | European Pat. Off. . |
| 3219575 | 2/1988 | Fed. Rep. of Germany . |
| 3711013 | 6/1988 | Fed. Rep. of Germany . |
| 3722590 | 12/1988 | Fed. Rep. of Germany . |
| 3800052 | 7/1989 | Fed. Rep. of Germany . |
| WO91/06254 | 5/1991 | PCT Int'l Appl. . |

Primary Examiner—Robert A. Hafer
Assistant Examiner—Brian E. Hanlon
Attorney, Agent, or Firm—Donald Brown

[57] ABSTRACT

A bone screw to be used in combination with a correction and supporting apparatus is provided. With such correction and supporting device the problem arises that when two vertebrae are expanded, the vertebra in between the vertebrae is shifted to the inside of the curvature of the spinal column. To correct or prevent such lateral shifting a bone screw is provided having a threaded shaft (60) and a segmented or fully spherically shaped head (61), an extension (62) having a support face (64) fitting on the head (61) being provided. An element (66) is connected to the extension (62). The element (66) serves to connect the extension with a rod (29, 30) at the correction and supporting apparatus. Element (66) and extension (62) are connected such that the distance between the support face and the element may be adjusted.

11 Claims, 3 Drawing Sheets

PEDICEL SCREW AND CORRECTING AND SUPPORTING APPARATUS COMPRISING SUCH SCREW

The invention relates to a pedicel screw which may be employed in particular in combination with a correcting and supporting apparatus for a spinal column, and to a correcting and supporting apparatus for a spinal column in combination with such pedicel screw.

UNFALLCHIRURGIE, Vol. 12 (1986), pages 68–79 discloses the mechanical principle for the dorsal stabilisation of the pectoral and lumbar spinal column by means of a correction and supporting apparatus. The brochure "Fixateur Interne für die Wirbelsäule, Original-Instrumente und -Implantate der Schweizerischen Arbeitsgemeinschaft für Osteosynthesefragen-AO" discloses a fixateur interne or internal fixation device. This device comprises two paris of so-called Schanz screws. A first pair thereof is screwed into the first vertebra through the arc roots (pediculus) on both sides and a second pair thereof is screwed into a second vertebra through the arc roots (pediculus) on both sides. The Schanz screws then have a shaft of a length of about 10 cm projecting from the vertebra. After mounting the four Schanz screws a parital reposition of the vertebra is already manually possible by means of the long projecting screw ends. Thereafter threaded rods are slipped into respective two Schanz screws lying on the same side of the superposed vertebra. Thereupon the projecting free ends of the Schanz screws are again operated and the threaded rods are arrested. Finally those parts of the Schanz screws which project beyond the threaded rods are cut off. Threrafter the fixateur is covered with the muscles and the skin and the cut is closed. Wherever the surgeon will discover the next day that an adjustment of the angular position of the vertebra would be required, such an adjustment is no longer possible, because the projecting parts of the Schanz screws which are necessary for adjusting the angular position have already been removed. Moreover, the rotational flexibility of the apparatus is low.

The DE 36 39 810 A1 discloses an implant for correction and/or stabilization of the spinal column. The implant comprises screws having a threaded shaft part and a receiving part which is rigidly connected with the threaded shaft part and turned away therefrom. A respective pair of screws has the end thereof rigidly connected with a tie rod through the corresponding receiving part. Moreover, the pair of screws is additionally connected through a tension rod at a point in a distance from the connection between the receiving part and the tie rod. In order to allow an adjustment of the axial direction of the screws and the vertebra receiving the screws in a direction deviating from the parallel position, the connection between the tension rod and both screws is adjusted such that a flexion or bending strain is exerted onto the tie rod or the tension rod. This results in an uncontrollable material stress which may, in course of time, lead to a destruction of the tension rod and/or the tie rod. This may result in unpredictable problems in the interior of the body.

It has been found that while adjoining vertebrae are expanded by such correcting and supporting device, the vertebra which is positioned between the vertebrae into which the screws of the device engage, is shifted into the direction where the expanded vertebrae are close to each other, which constitutes an unwanted effect.

It is an object of the invention to provide a pedicel screw to compensate this effect in combination with a correction and supporting apparatus for the spinal region, and to provide a correcting and supporting apparatus in particular for the spinal column employing such pedicel screw, which prevents or compensates for the shifting of a vertebra transverse to the spinal column apparatus when such correcting and supporting apparatus is employed.

A correcting and supporting device to solve this problem is indicated in claim 1.

Additional embodiments are indicated in the subclaims.

Further features and advantages will become apparent from the description of the embodiments and the figures, in which.

Figure 1:
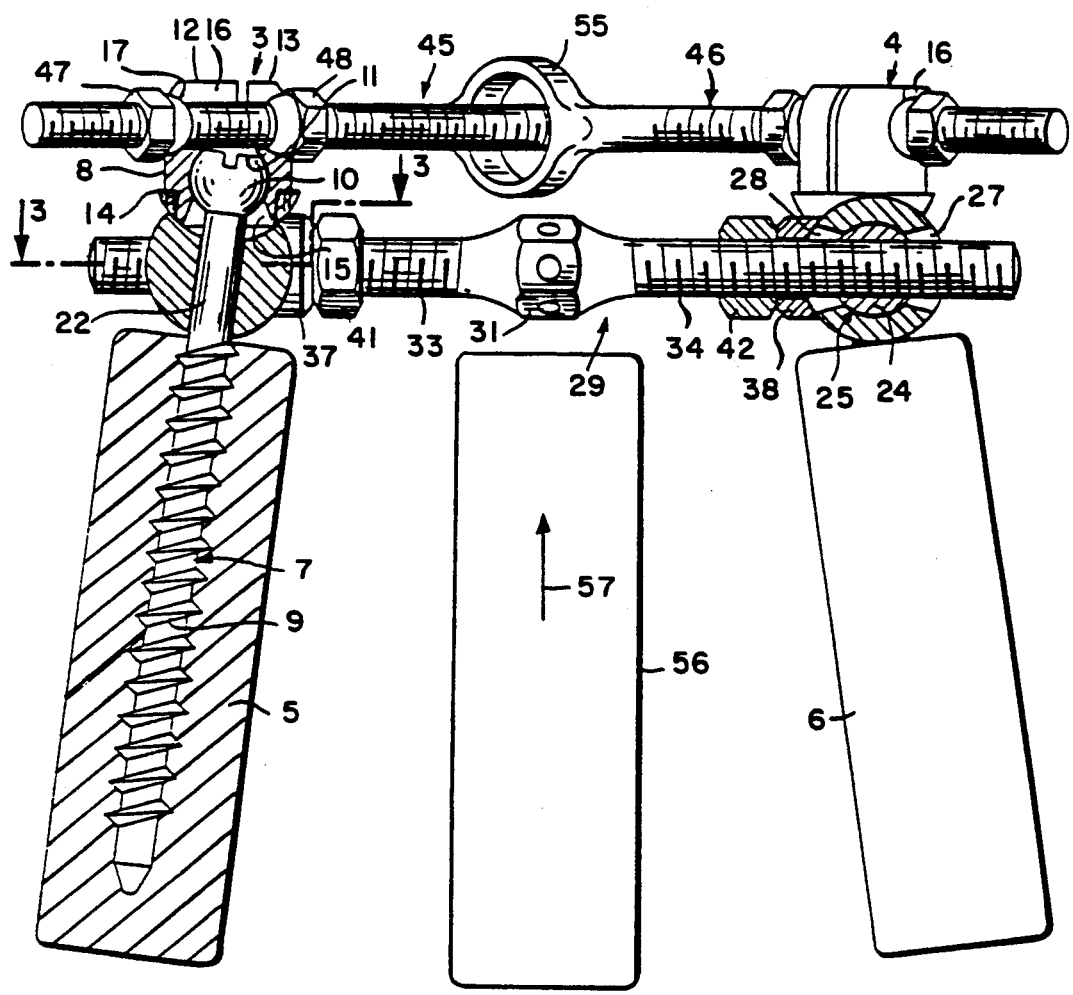
FIG. 1 is a partially sectional side view of a correcting and supporting apparatus.
Figure 3:
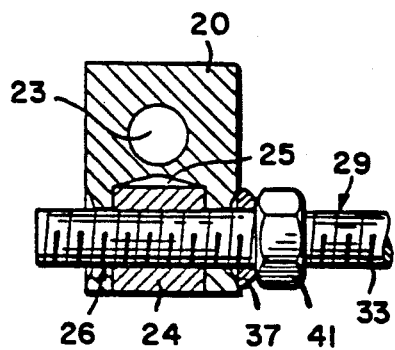
FIG. 3 is a sectional view along line III/III of FIG. 1.

The correction and supporting apparatus comprises four screws 1–4 forming bone screws. In mounting the correction and supporting apparatus for stabilization of the spinal column the first pair of screws 1, 3 is screwed into the arc roots (pediculi) in a schematically indicated first vertebra 5. The second pair of screws 2, 4 is correspondingly screwed into the arc roots (pediculi) of an also schematically indicated second vertebra 6.

Each one of the respective screws 1–4 comprises a threaded shaft member 7 having a threaded portion 9 and a spherical segment shaped head 10 provided at the head end of the threaded shaft member, as well as a receiver member 8. The head has a plane surface 11 extending perpendicular to the axis of the threaded portion and being positioned at the side of the head facing away from the threaded portion 9. The plane surface further comprises at a position coaxial with the threaded portion a slot or a similar engagement providing member for a screw driver for screwing the screw into a vertebra.

The receiver member 8 comprises two head halves 12, 13 as well as a retaining ring 14 holding together the two head halves. Each head half comprises a hollow spherical segment shaped portion on the inner side thereof which faces the other head half, the inner radius of the hollow spherical segment shaped portion corresponding to the outer radius of the spherical segment shaped head 10. A neck portion 15 is adjacent to the spherical segment shaped portion. The neck portion is formed as a segment of a hollow spherical portion and is formed to be outwardly divergent from the spherical segment shaped portion. The axis of the neck portion passes through the center of the hollow spherical segment shaped portion. The spherical segment shaped portion has, on the side thereof opposite to the neck portion, a receiver groove 16 which extends perpendicular to the axis of symmetry of the neck portion and of the spherical segment shaped portion and which has a recess 17 formed in the outside thereof which is turned away to the other head half. The width of the receiver groove 16 is selected such that a threaded rod to be received may loosely be passed therethrough. In this manner the receiver member may freely pivot within a cone angle around the axis of the threaded shaft member 7 and may freely rotate around the axis of the screw for adjusting the direction of the groove.

Each screw comprises at a position between the receiver member 8 and the threaded portion 9 a cylindrical member 18–21 extending perpendicular to the screw axis. A bore 23 extends through the cylindrical member at one end thereof in a direction perpendicular to the cylinder axis. The diameter of the bore 23 is selected such that a neck 22 of the respective screw between the head and threaded portion thereof can properly be fitted into the bore. A bore 25 receiving a bolt 24 is provided at the other side of the cylindrical member coaxial with the axis thereof. The bolt 24 comprises a threaded bore formed perpendicular to the axis of the bore and to the cylinder axis. The dimensions of the bolt are selected such that it can be freely rotated around its own axis within the bore 25. A further bore 26 is provided in the cylinder in a direction perpendicular to the bore 23 and to the bore 25. This further bore 26 is coaxial with the threaded bore in the bolt such that a screw can be screwed therethrough into the bolt 24. Both ends of the bore 26 have conically widened portions 27, 28 in a direction parallel to the screw axis which allow a pivoting movement of the screws received therein around the longitudinal axis of the cylindrical member within a region defined by the conical widened portions.

Figure 2:
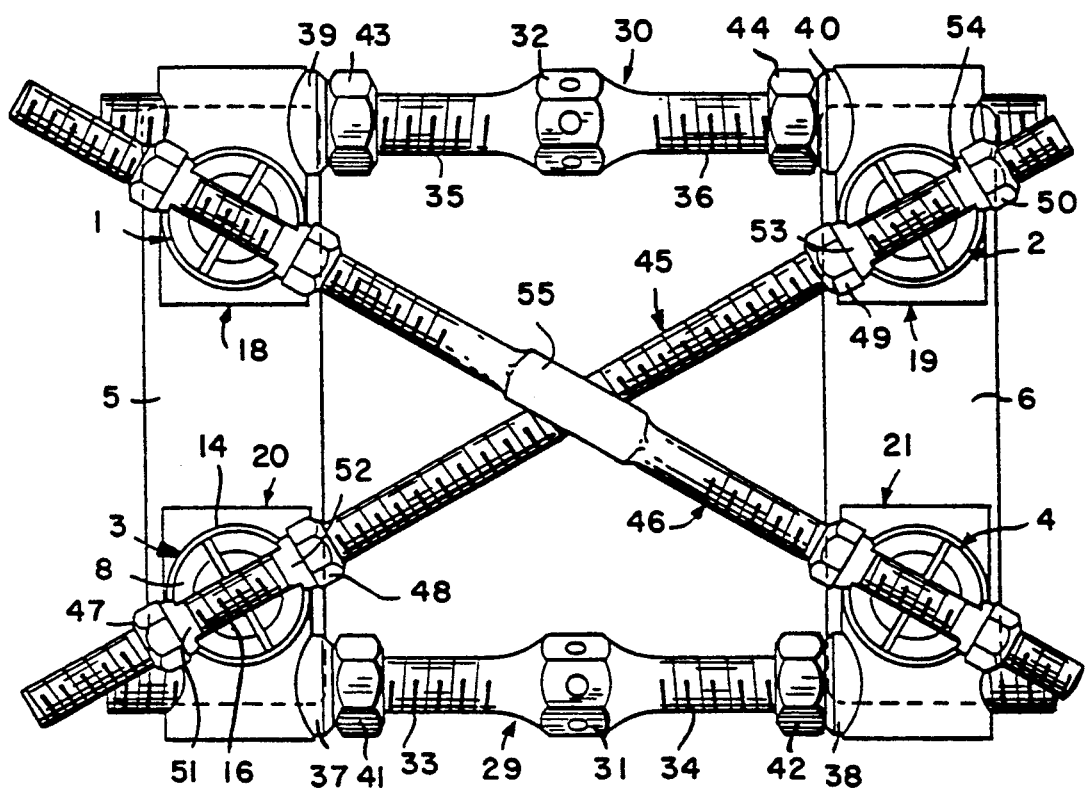
FIG. 2 is a top view of the apparatus shown in FIG. 1.

The correction and supporting apparatus further comprises a pair of threaded rods 29, 30. These rods have a central portion thereof formed as a coaxial hexagon portion 31, 32 for engagement with a wrench and further threaded portions 33, 34; 35, 36 adjacent thereto on both sides. The respective opposite threaded portions 33, 34 and 35, 36 of a threaded rod are formed as oppositely directed right-handed threads and left-handed threads, resp. An intermediate member 37–40 acting as a washer is provided for each threaded portion. The intermediate member is formed with a plane surface on the side thereof facing the hexagon and with a hollow cylindrical segment shaped surface on the opposite side thereof. The curvatures of the latter surface corresponds to the curvatures of the outer surface of the respective cylindrical member 18–21. A respective nut 41–44 is provided between the hexagon portion and the intermediate member. As may be best seen from FIG. 2, a threaded rod 29 is connected with the two screws 3, 4 to be arranged on one side of the spinal column through the connecting cylindrical members 20, 21 by screwing the threaded portions into the bolts 24. The nuts 41–43 are not yet tightened, such that there is sufficient looseness and the screws may be screwed into the vertebrae. The threaded rod 30 is connected with the screws 1 and 2 through the associated cylindrical members in corresponding manner. After screwing the screws 1–4 into the associated parts of the vertebrae the nuts 37–40 are loosely tightened, such that a distance between the opposite screws 1, 2 and 3, 4, resp., is defined.

Further threaded rods 45 and 46 are provided. The threaded rod 45 is a simple threaded rod having two pairs of nuts 47, 48; 59, 50. The pairs of nuts have spherical segment shaped portions 51, 52 and 53, 54, resp., facing each other and being formed coaxial with the threaded rod. The respective head halves of the receiver member 8 comprise, as may be best seen from FIG. 1, spherical segment shaped recesses 17 formed coaxially with the corresponding receiver groove 16. The diameter of the threaded rod is selected such that it can just be inserted into the receiver grooves of the receiver members of the screws 1 and 4. The threaded rod 46 differs from the above described threaded rod 45 only in that it has a portion forming an eye 55 in the central region thereof. Otherwise the threaded rod is formed such that it can be inserted into the receiver groove of the screws 2 and 3. The eye 55 serves to pass the threaded rod 46 therethrough such that both screws or rods can be connected with the screws 1, 4 or 2, 3, resp., in virtually the same plane. Owing to the possibility of pivoting the receiver portions relative to the screws the insertion of the threaded rods 45, 46 is easily possible. After insertion the respective pairs of screws and rods are tightened for provisionally locking the threaded rods in relation to the receiver portions.

In operation it is started with drilling holes into the respective pairs of vertebra 5, 6 for receiving the screws 1–4. Thereafter a corresponding distance for the screws 1, 2 and 3, 4, resp., is adjusted by means of the threaded rods 29, 30 in dependence on the distance of the bores corresponding to the screws 1, 2 and 3, 4, resp. The screws 1–4 are then screwed into the prepared holes. Thereafter the threaded rods 45 and 46 are fitted into the associated grooves. The angular position of the vertebrae 5 and 6 in relation to each other is then adjusted by operating the nut pairs 47, 48 and 49, 50, resp. Simultaneously or in alternation therewith a change in distance may be obtained by adjusting the threaded rods 29 and 30. Following the desired adjustment the nuts 41–44 and the pairs of nuts 47, 48 and 49, 50 are tightened. The above described design enables the exact longitudinal and angular adjustment of the vertebrae and the repetition of such an adjustment at a later time with the same apparatus. Owing to the crossing threaded rods a high resistance to torsional forces is obtained. Since no parts of the apparatus are removed even after the adjustment operation, the apparatus remains fully operative for future readjustments.

As can be seen from FIG. 1, the vertebra 56 in between the vertebrae 5 and 6 to be expanded, is shifted in the direction of arrow 57 to the side of the spiral column where the expanded vertebrae are closer to each other, i.e. towards the correction and supporting device.

Figure 4:
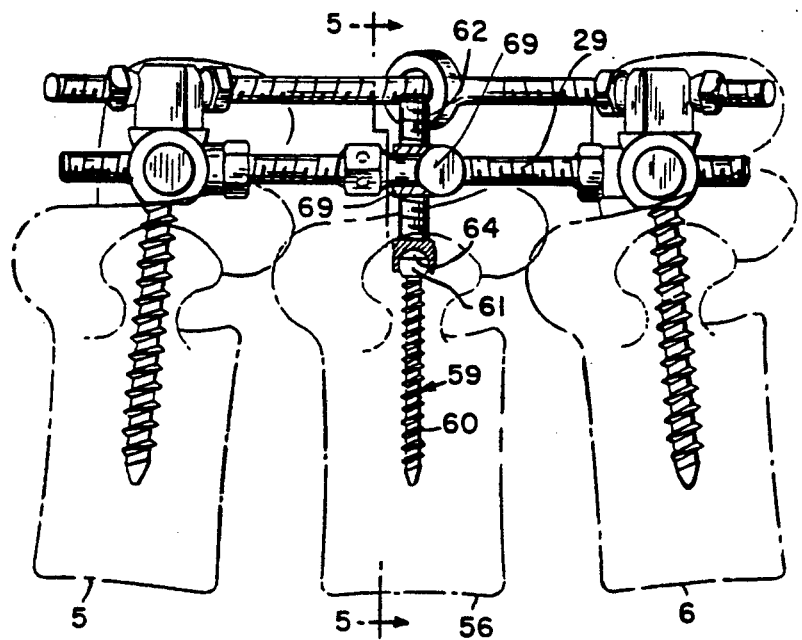
FIG. 4 is a view similar to FIG. 1 with a pedicel screw.
Figure 5:
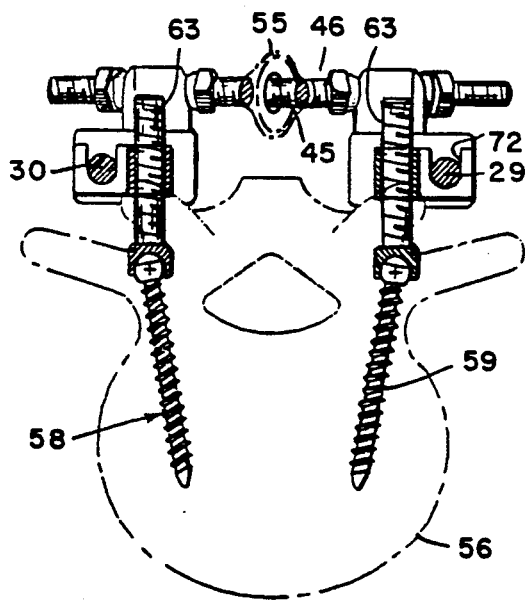
FIG. 5 is a sectional view along lline V/V.

As shown in FIGS. 4 and 5, pedicel screws 58, 59 are supported on each of the threaded rods 29 and 30 in the region of the vertebra 56.

Figures 6, 7:
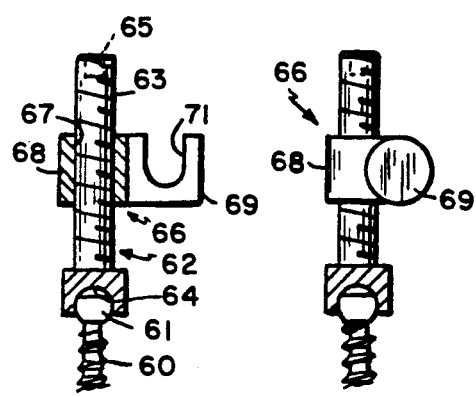
FIG. 6 is a partially sectional side view of the pedicel screw.
FIG. 7 is a side view of the pedicel screw rotated by 90° with respect to FIG. 6.
Figure 8:
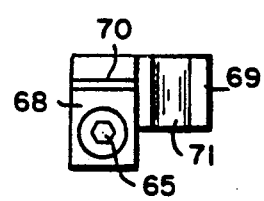
FIG. 8 is a top view of the pedicel screw.

In the following, the design of such pedicel screw is described. The pedicel screw has a threaded shaft 60 and a segmented spherical or fully spherical head 61 on its free end, as well as an extension 62 to be positioned thereon. The extension comprises a threaded shaft 63 having a head forming a concave support 64. Preferably, the concave support is spherically shaped, its radius corresponding approximately to the radius of the spherical part of the head 61. Opposite to the support 64 the threaded shaft is provided with a slit 65 into which a screw driver may be engaged. An element 66 is connected with the threaded shaft. It comprises a first part 68 and a second part 69 connected thereto. The first part has a rectangular shape and a threaded bore, the thread corresponding to the external thread of the threaded shaft 63 and being screwed thereon, as can be seen from FIGS. 6 and 7. The second part 69 is provided with a pivot 70 fitting into a corresponding pivot hole provided in the first part 68. The axes of pivot hole and pivot 70 extend transversely to the longitudinal axis of the threaded shaft 63, preferably in rectangular direction thereto. The diameter of pivot 70 and pivot hole correspond to each other such that the second part 69 may be rotated around the pivot axis. The second part is provided with a U-shaped groove, its plane of symmetry extending perpendicularly to the longitudinal axis of pivot 70. The width of said groove 71 is dimensioned such that threaded rod 29 or 30, resp., may be inserted therein. The base of the U-shaped groove is provided with an internal thread corresponding to the external thread of the threaded rods 29, 30 to be inserted. As indicated in FIG. 5, a screw 72 may be provided at the upper rim of the groove in order to secure the inserted threaded rod 29, 30 in the groove. The interior thread engages with the thread on the inserted rod, thereby preventing slipping of part 62 in lateral direction.

As can best be seen from FIG. 5, in operation the threaded shaft 60 and head 61 are screwed into the vertebra 56. For this purpose, the head is provided with a plane and a slit for engaging a screw driver. After the screw has been screwed in, the extension 62 with its support 64 is put on the head 61. By rotating the threaded shaft 63 the distance of the element 66 with respect to the head 61 may be adjusted such that the threaded rods 29, 30 are resting on the base of the groove 71. Adjusting the axis of groove 71 to be parallel with the axes of threaded rods 29, 30 is easy, since the second part 69 may be rotated around the axis of pivot 70 and also be rotated and shifted together with the threaded shaft within a cone around the center of the sperical section of head 61. Subsequently, the threaded shafts 63 are rotated until the vertebra 56 is returned to the desired position contrary to the direction of arrow 57 in order to compensate for the shifting caused by the soft bone craft. Alternatively, this positioning may be done prior to the expansion such that a shifting in the direction of arrow 57 caused by the soft bone craft is prevented from the beginning.

We claim:

1. A correction and supporting apparatus for a spinal column having vertebrae (5, 6, 56) comprising two pairs of screws (1, 3; 2, 4), each screw having a threaded shaft (7) and a receiver member (8), each pair of screws (1,3; 2, 4) to be anchored in a vertebra, a first pair of threaded rods (45, 46) each of said rods (45, 46) connecting with two of said screws (1, 4; 2, 3) on a first connecting point on said two of said screws respective receiver member (8), and a second pair of threaded rods (29, 30) each respective one of said second pair of threaded rods (29, 30) connected to two of said screws (3, 4; 1, 2) on a connecting point shifted with respect to said first connecting point towards said threaded shaft (7) of each connected screw, said first and second pairs of rods (45, 46, 29, 30) for bridging at least one further vertebra (56) in between said vertebrae (5, 6), a pedicel screw (58, 59) which is adjustable such that a thrust may be applied on said at least one further vertebra (56) in a direction to move it away from said correction and supporting apparatus.

2. The apparatus of claim 1, wherein a first pair of screws is adapted to be screwed into opposite first and second sides of a first vertebra, and a second pair of screws is adapted to be screwed into the corresponding first and second sides of the second vertebra.

3. The apparatus of claim 1, wherein said first pair of threaded rods is respectively connecting two of said screws which are anchored in different vertebrae and diagonally opposing each other, whereas said second pair of threaded rods is respectively connecting two of said screws anchored in different vertebrae but directly opposing each other.

4. The apparatus of claim 3, wherein one rod of said first pair of threaded rods comprises an eye for passing therethrough the second rod of said first pair of rods.

5. The apparatus of claim 1, wherein each of said screws comprises a threaded shaft, said receiver member for receiving said threaded rods being pivotably connected 6. The apparatus of claim 5, wherein the threaded shaft portion and the receiver member of said screws are interconnected by a joint member in such a way that the receiver member is free to move in relation to the threaded shaft portion around a first and a second axis, said second axis extending transversely to said first axis.

7. The apparatus of claim 1, wherein the ends of said second pair of threaded rods are provided with threads having opposite pitch.

8. The apparatus of claim 1, wherein said pedicel screw comprises:
a threaded shaft and a segmented or fully spherically formed head,
an extension for said head having on one end a support face fitting on said head and an element to be connected to one of said threaded rods,
said element and said extension being connected such that the distance between said one end and said element is adjustable.

9. The apparatus of claim 8, wherein said extension is formed as a threaded shaft having a support face on one end, and wherein said element is provided with a threaded bore engaging said threaded shaft.

10. The apparatus of claim 8, wherein said element comprises a first part connectable with said extension, and a second part connectable with said one of said threaded rods, said first and said second parts being pivotable around an axis, said axis extending transversely to the axis of said threaded shaft.

11. The apparatus of claim 10, wherein said second part is provided with a groove for receiving one of said threaded rods.

* * * * *